United States Patent [19]

Dubur et al.

[11] Patent Number: 4,769,382

[45] Date of Patent: Sep. 6, 1988

[54] PREPARATION FOR PREVENTING AND TREATMENT OF SKIN RADIATION BURN LESIONS

[75] Inventors: Gunar Y. Dubur; Egils A. Biseniex, both of Riga; Yan R. Uldrikis, Elgava; Evgeny V. Ivanov, Leningrad; Tatyana V. Ponomareva, Leningrad; Gennady N. Merkushev, Leningrad; Jury O. Yakubovsky-Lipsky, Leningrad, all of U.S.S.R.

[73] Assignees: Institut Organischeskogo Sinteza Leningradsky Nauchno-Issledovatelsky Institut, Riga; Radiatsionnoi Gigieny, Leningrad, both of U.S.S.R.

[21] Appl. No.: 908,394

[22] Filed: Sep. 17, 1986

[51] Int. Cl.$^4$ ............................................. A61K 31/24
[52] U.S. Cl. .................................................... 514/356
[58] Field of Search ...................... 514/356; 546/321

[56] References Cited

U.S. PATENT DOCUMENTS 4,622,332 11/1986 Wehinger et al. .................. 514/356

OTHER PUBLICATIONS

Chemical Abstracts, 87:150487z, (Sprurzs et al), 1977.
Chemical Abstracts, 94:96326a, (Duburn et al), 1981.

Primary Examiner—Leonard Schenkman
Attorney, Agent, or Firm—Burgess, Ryan & Wayne

[57] ABSTRACT

A preparation for prevention and treatment of radiation burning lesions of the skin comprising an active principle, viz. 2,6-dimethyl-3,5-diethoxycarbonyl-1,4-dihydropyridine of the following formula:

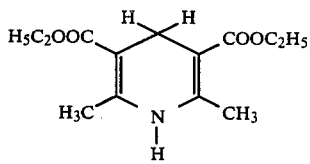

and a pharmaceutically acceptable diluent.

5 Claims, No Drawings

PREPARATION FOR PREVENTING AND TREATMENT OF SKIN RADIATION BURN LESIONS

FIELD OF THE INVENTION

The present invention relates to medicine and, more specifically, it relates to a novel pharmaceutical preparation for prevention and treatment of skin radiation burning lesions caused by both ionizing and non-ionizing radiation. The preparation is useful for protection of patient's skin in the course of radiation therapy in clinics, for protection of the personnel's hands upon handling and manipulations with sources of ionizing radiation, as well as for prophylaxis and treatment of UV and thermal burns.

DESCRIPTION OF THE PRIOR ART

Known in the art the present time are various preparations for the treatment of radiation burns such as dimethylsulphoxide, mexamine (5-methoxytryptamine hydrochloride), cystamine ($\beta$-mercaptoethylamine), pantenol, ionol (4-methyl-2,6-ditertiarybutylphenol), methyluracyl liniment and the like (cf. M. S. Bardychev, A. F. Tsyb, Local Radiation Lesions, Moscow, Meditsina Publishers, 1985, pp. 55-67; E. V. Ivanov et al. "Quantitative Assessment of the Effect of Certain Skin Protectors" Meditsinskyaa Radiologiya, Moscow, 1983, No. 7, pp. 40-44).

However, administration of these preparations fails to improve the effectiveness of radiation therapy through elevation of doses of the tumor in radiation. Furthermore, these preparations possessing a certain preventive effect are virtually ineffective for therapeutical applications. Due to their toxicity they are inapplicable either as semi-cosmetic preventive agents or for a daily application onto the skin of the personnel's hands for operation with sources of ionizing radiation. These preparations are ineffective in respect of non-ionizing radiation.

Known in the art is a compound, viz. 2,6-dimethyl-3,5-diethoxycarbonyl-1,4-dihydropyridine of the following structure:

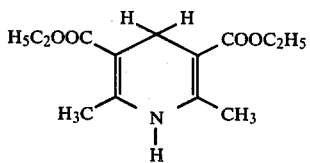

(cf. USSR Inventor's Certificate No. 300465, published 1971).

However, the use of this compound as an active principle for a preparation intended for prophylaxis and treatment of skin radiation burning lesions is unknown in the art. The preparation according to the present invention is novel and hitherto unknown in the literature.

SUMMARY OF THE INVENTION

It is an object of the present invention to provide a novel preparation for prevention and treatment of skin radiation burning lesions, which has low toxicity, has a high effectiveness for protecting the skin against both ionizing and non-ionizing radiation and allows the use of increase radiation doses.

This object is accomplished by providing a preparation according to the present invention for the treatment and prevention of radiation skin burning lesions which incorporates an active principle and a pharmaceutically acceptable diluent, in accordance with the present invention, and comprises as an active principle 2,6-dimethyl-3,5-diethoxycarbonyl-1,4-dihydropyridine of the following formula:

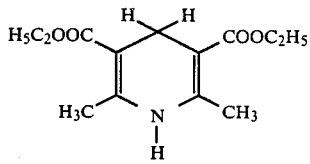

The preparation according to the present invention is preferably used as an ointment with a content of the active principle ranging from 5 to 10% by weight. As the pharmaceutically acceptable diluent it preferably incorporates vaseline or lanolin It is advisable to employ the preparation according to the present invention as a preventive agent for prophylaxis of radiation skin lesions and as a pharmaceutical agent for the therapy of the following diseases: acute radiodermatites in all stages of their development; chronical radiodermatites of different location including connecting skin regions (intergluteal folds, perineal region, lips, etc.), ultra-violet (UV) burns of skin, thermal burns chemical burns (those of eyes in particular).

The preparation according to the present invention is a local-action preparation; it has a clearly pronounced antioxidant activity, normalizes oxidation-reduction processes in irradiated tissues, hinders the development of processes of peroxy-type oxidation of lipids in cellular membranes and their disintegration, prevents the development of structural changes in cells of epiderm and subcellular structures, lowers the permeability of capillaries, exhibits a detoxifying effect, facilitates normalization of the tissue metabolism and stimulates regeneration processes.

The preparation according to the present invention in the form of a 5-10% ointment features both radioprotective and therapeutic properties. The preparation according to the present invention partly penetrates through the skin and gets deposited therein. When applied onto the skin prior to irradiation, it improves the radioresistance thereof and prevents or minimizes the origination of radiation dermatitis: erythema, wet and dry desquamation. In the case of appearance of radiation dermatites the preparation according to the present invention eliminates edema, hyperemia, pruritus, pain and burning irritation of the skin, accelerates its healing and facilitates a rapid normalization of tissue and cellular structures. The preparation according to the present invention is of low toxicity, it does not have mutagenic, embryotoxic and carcinogenic properties, does not provide a radioprotective effect on the tumor tissue and is rapidly metabolized to an oxidized state and withdrawn from the organism.

DETAILED DESCRIPTION OF THE INVENTION

The preparation according to the present invention has been experimentally studied on animals and in clinics on human beings.

A comparative study of the therapeutic and preventive effect of the preparation according to the present invention has been also carried out in parallel to a number of prior-art pharmaceutical preparations and radioprotectors (mexamine, custamine, dimethylsulphoxide, pantenol, methylracyl liniment, ionol).

The determination of a local radioprotective effect of the preparation according to the present invention has been conducted on random-bred albino rats of both sexes and a standard mass upon β-irradiation with $E_{app}^{eff}$ (effective energy)=0.76 MeV (3 groups of animals and X-ray irradiation with $E_{app}^{eff}=8$ keV. The effect of β-radiation was studied on the skin of floors of the auricle by way of using a flexible applicator containing a source of a soft beta-radiation of $^{204}Tl$. The maximum energy (E) in tissues is 3 mm. The dose rate of the employed sources was 7.2 and 12 Gy/h. The exposure time was 5 to 11 hours depending on the source activity and time of its exploitation (the half-life period for $^{204}Tl$ is 3.9 years.). The dose of radiation was 60 Gy (Gray), the absorbed dose at the level of the basal layer determined by calculation being 40 Gy. The preparation according to the present invention was applied in a thin layer onto the surface of one of the auricles in the form of a 5% ointment 20 minutes before irradiation, while the other auricle was greased with vaseline and served as control. The dosage of the preparation was effected at the rate of 100 mg of the final pharmaceutical preparation (5 mg of the active principle) per 1 cm$^2$ of the skin. For comparison of the radioprotective effect in one of the groups of animals auricles were greased with dimethylsulphoxide 20 minutes prior to irradiation. The results of tests of groups 1-3 are shown in Table 1 hereinbelow.

The determination of the radioprotective effect of the preparation according to the present invention in the case of X-ray irradiation was effected on the skin of paws. Irradiated were 9 groups of animals (4-8 animals in each group).

The irradiation was effected using an X-ray source (radiator) at the current of 62 μA and the anode voltage of 26 kV. The effective energy $E_{eff}$ for these conditions was 8 keV. The absorbed dose in the skin layer of 1 mm thickness was about 61% of the input dose.

By means of a special adapter put on the barrel of the source (radiator) the hind limbs of a rat were rigidly secured at the distance of 1 cm of the X-ray tube which ensured standard irradiation conditions and shielding of the other parts of the rat's body. Irradiated were skin regions of 90 mm$^2$ on each limb. The rate of the exposure dose was 11.6 Gy/min (the dose for the surface area—30 Gy).

The extent of the skin radioprotective effect was assessed by a number of clinical dermatological tests by recording visual observations over the progress of radiation dermatitis. The tests were effected by the blank method at strictly predetermined hours of the day by a team of specialists. The form of dermatitis in each irradiated skin locus (moist or dry desquamation, intense and weak erythema) was recorded daily by means of special codes over the entire observation period. The number of the same codes for every irradiated skin locus (frequencies of features) were summed up and a group mean value was calculated. The number of animals in each group was not less than 7 and the number of irradiated skin loci was within the range of from 12 to 14.

The thus-obtained values were statistically processed and evaluated by means of the Student criterion. Therefore, the severity of radiodermatitis was quantified by means of the following tests:

(a) duration of periods of light and severe erythema;
(b) duration of periods of moist and dry desquamation.

Groups 4, 5 and 6 were irradiated in the dose of 20 Gy, groups 7 through 12—in the dose of 30 Gy. The paws of control animals (groups 4-7) 20 minutes prior to irradiation were greased with vaseline. The rats of groups 6, 8, 9 and 10 were greased, on the skin of paws of hind limbs, with the preparation according to the present invention 20 minutes before the irradiation in the form of a 5% emulsion: on vaseline—groups 6 and 8, on castor oil—group 9, on lanolin—group 10. For all groups of animals an appropriate control with irradiation was provided but without using the preparation according to the present invention, as well as control with the use of castor oil and vaseline, and with the use of dimethylsulphoxide in the form of a 5% solution. The test results are shown in Table 1 hereinbelow.

It follows from Table 1 that the preparation according to the present invention exhibits a reliable redioprotective activity both for β-irradiation and for X-ray irradiation of skin in injuring doses (20-30 Gy). The absorbed dose on the basal layer under β-irradiation is, according to calculations, about 40 Gy. Under soft β-irradiation the preparation according to the present invention sharply reduces the duration of all stages of dermatitis from 10.8 to 3.7 days (by about 3 times), while the duration of a severe erythemic response—even by 7 times. Desquamation caused by β-irradiation is fully prevented. A sole sign of dermatitis remains as a weak erythema. Effectiveness of the preparation according to the present invention as determined according to these parameters is superior to all other known preparations.

As it is seen from Table 1, upon X-ray irradiation in the dose of 20 Gy where the response is limited predominantly to erythema, the preparation according to the present invention diminishes this response by more than half (from 50 hours in the control to 22 hours in the experiment). Upon irradiation in higher doses (30 Gy) application of the preparation according to the present invention not only reduces erythema, but considerably (by 31%) shortens the duration of the moist desquamation period. In this case ulcerations is less pronounced and radiodermatitis comes into an easier form with prevailing dry desquamation. The use of castor oil, lanolin and hydropholic bases ensuring a better penetration of the preparation into the skin makes it possible to improve radioprotective effeciency of the preparation according to the present invention. The manifestation moist dermatitis in this case is diminished by 50-60%.

TABLE 1

Results of evaluation of the radioprotective effect of the compound according to the present invention on rat's skin

| No. of group of animals 1 | Preparation 2 | Type of irradiation 3 | Dose in Grays 4 | Number of loci 5 |
|---|---|---|---|---|
| 1. | Control | β-radiation $E_{eff}=$ 0.76 MeV | 60 | 24 |
| 2. | Dimethylsulphoxide | | 60 | 3 |
| 3. | Compound of the invention | | 60 | 6 |

TABLE 1-continued

Results of evaluation of the radioprotective effect
of the compound according to the present invention on rat's skin

| 4. | Control | X-ray radiation, $E_{eff} =$ 8 keV | 20 | 16 |
|---|---|---|---|---|
| 5. | Dimethylsulphoxide | | 20 | 14 |
| 6. | Preparation of the invention | | 20 | 14 |
| 7. | Control | | 30 | 14 |
| 8. | Preparation of the invention | | 30 | 14 |
| 9. | Preparation of the invention | | 30 | 8 |
| 10. | Preparation of the invention | | 30 | 8 |
| 11. | Castor oil | | 30 | 10 |
| 12. | Vaseline | | 30 | 10 |

| No. of group of animals 1 | Duration of response (days) X ± m | | | | Diminution of response, % of the control | | |
|---|---|---|---|---|---|---|---|
| | Erythema | | Desquamation | | Erythema | Desquamation | |
| | weak 6 | severe 7 | dry 8 | moist 9 | severe 10 | dry 11 | moist 12 |
| 1 | 2.6 ± 0.4 | 2.2 ± 0.8 | 2.2 ± 0.7 | 0.6 ± 0.4 | 0 | 0 | 0 |
| 2 | 1.7 ± 1.7 | 1.3 ± 1.7 | 1.0 ± 1.2 | 0.0 ± 0.0$^x$ | — | — | 100 |
| 3 | 1.7 ± 0.5 | 0.3 ± 0.3$^{xxx}$ | 0.3 ± 0.2$^{xx}$ | 0.0 ± 0.0$^x$ | 86 | 86 | 100 |
| 4 | 1.8 ± 0.3 | 0.3 ± 0.1 | 5.6 ± 0.5 | 0.2 ± 0.2 | 0 | 0 | 0 |
| 5 | 1.6 ± 0.3 | 0.4 ± 0.3 | 2.8 ± 0.6$^x$ | 0.1 ± 0.1 | — | 50 | — |
| 6 | 0.8 ± 0.3$^x$ | 0.1 ± 0.1$^x$ | 4.9 ± 0.5 | 0.2 ± 0.2 | 67 | — | — |
| 7 | 1.7 ± 0.3 | 1.9 ± 0.3 | 4.5 ± 0.3 | 4.2 ± 0.5 | 0 | 0 | 0 |
| 8 | 1.8 ± 0.1 | 0.6 ± 0.0$^x$ | 5.0 ± 0.3 | 2.9 ± 0.4$^x$ | 21 | — | 31 |
| 9 | 3.0 ± 0.4$^x$ | 1.1 ± 0.5 | 3.7 ± 0.4$^x$ | 1.7 ± 0.5$^{xx}$ | 42 | 18 | 60 |
| 10 | 3.5 ± 1.3 | 1.1 ± 0.5 | 6.9 ± 0.7$^x$ | 2.0 ± 0.5$^x$ | 42 | — | 52 |
| 11 | 1.3 ± 0.2 | 1.6 ± 0.3 | 6.6 ± 0.3 | 4.7 ± 1.0 | — | — | — |
| 12 | 1.5 ± 0.4 | 1.8 ± 0.4 | 4.8 ± 0.5 | 3.9 ± 0.9 | — | — | — |

Note:
$^x$differences with the control are statistically certain with probability of not less than 0.
$^{xx}$with probability of not less than 0.99;
$^{xxx}$with probability of not less than 0.999.

Apart from the effect on duration of radiodermatitis signs, in these experiments the reduction of the frequency of appearance of pathological reactions in the group of animals was noted. Thus, upon irradiation in the dose of 30 Gy the number of loci where the reaction of moist desquamation was absent increased by 2.5 times owing to the use of the preparation according to the present invention which corresponds to reduction of the dose effect by 3 Gy. Upon irradiation in the dose of 20 Gy the frequency of appearance of erythema responses and those of moist desquamation is reduced by 1.5-2 times. The test results are shown in Table 2 hereinbelow.

TABLE 2

Reduction of frequency of radiation responses on the sole skin upon radiation in the dose of 20 Gy

| Compound | Number of animals | Frequency of response appearance, % | | |
|---|---|---|---|---|
| | | Erythema | | Moist des- |
| | | weak | severe | quamation |
| Control | 14 | 72 | 21.4 | 14.3 |
| Preparation of the present invention | 14 | 36 | 14.3 | 7.1 |

The pharmacological activity of the preparation according to the present invention depends to a considerable extent on the concentration of the active principle, as well as on the physico-chemical properties and dissolving capacity of the diluent which can contribute to an enhancement or weakening of the preparation interaction with cellular membranes. For this reason, it is necessary to carry out a comparative study of the preparation according to the present invention for different ointment bases.

The determination of the radioprotective effect was carried out on 42 random-bred albino rats aged 4 months with a mass of 160–180 g on 80 test regions of skin in experiments with a local X-ray irradiation of $E_{eff}=8$ keV on 4 groups of animals.

The preparation according to the present invention was used in the form of 10% and 2.5% emulsions on a hydrophilic base (groups 2 and 3), in the form of a 5% emulsion on a colloidal base (group 4) applied onto the skin 20 minutes before irradiation. Group 1 served as control.

As a result of the study it has been found that the preparation according to the present invention has a specific activity which is displayed and remains at a sufficiently high level for different ointment bases including hydrophilic ones. The results of tests of various ointments of the preparation according to the present invention are shown in Table 3.

TABLE 3

Results of a comparative evaluation of the radioprotective effect produced by the preparation according to the present invention in the form of different ointments upon irradiation in the dose of 30 Gy.

| Test compound | Duration of the reaction, days, X ± m | | | | Total duration, days |
|---|---|---|---|---|---|
| | Erythema | | Desquamation | | |
| | weak | severe | dry | moist | |
| 1. Control | 1.6 ± 0.2 | 3.1 ± 0.2 | 4.0 ± 0.5 | 5.1 ± 0.4 | 13.9 ± 0.6 |
| 2. Compound of the invention on a hydrophilic base (10% emulsion) | 1.7 ± 0.3 | 3.3 ± 0.3 | 4.5 ± 0.3 | 4.5 ± 0.7 | 14.0 ± 0.8 |

TABLE 3-continued

Results of a comparative evaluation of the radioprotective effect produced by the preparation according to the present invention in the form of different ointments upon irradiation in the dose of 30 Gy.

| Test compound | Duration of the reaction, days, $X \pm m$ | | | | Total duration, days |
|---|---|---|---|---|---|
| | Erythema | | Desquamation | | |
| | weak | severe | dry | moist | |
| 3. Compound of the invention on a hydrophilic base (2.5% emulsion) | $1.9 \pm 0.3$ | $1.9 \pm 0.3^{xx}$ | $4.8 \pm 0.5$ | $1.9 \pm 0.4^{xxx}$ | $10.5 \pm 0.5^{xxx}$ |
| 4. Compound of the invention on a colloidal base (5% emulsion) | $1.4 \pm 0.2$ | $2.3 \pm 0.3^{x}$ | $6.2 \pm 0.6^{x}$ | $2.1 \pm 0.6^{xxx}$ | $12.0 \pm 0.7^{xxx}$ |

Note:
Differences are statistically certain at:
$^{x}(p < 0.5)$;
$^{xx}(P < 0.01)$;
$^{xxx}(P < 0.001)$.

Ointment bases do not reveal any significant specific radioprotective effect. They, however, can enhance the protective effect of the preparation according to the present invention, increasing concentration of the active principle to 10% lowers specific activity.

For a comparative evaluation the data obtained in a similar experiment with a number of known preparations (castamine, ionol, dimethylsulphoxide), as well as with eugenol (3-methoxy-4-hydroxyallylbenzene) and castor oil were used.

Ionol (4-methyl-2,6-ditretbutylphenol) is employed as control as an analog-antioxidant featuring a radioprotective activity.

The test results are shown in Table 4 hereinbelow.

The preparation according to the present invention has been also tested for its therapeutic effect on radiation dermatitides. The therapeutic effect was studied on 42 skin regions in experiments on random-bred albino rats of both sexes with a mass of 230–250 g. Radiation dermatites were induced by X-ray irradiation of the skin. The irradiation was conducted using an X-ray unit at the current of 50 $\mu$A and the anode voltage of 26 kV. Under these conditions $E_{eff}$ is 8 keV, the absorbed dose in the skin layer of 1 mm thickness is about 61% of the input dose. Skin regions of 90 mm$^2$ on each limb were subjected to irradiation. The exposure dose rate was 12.5 Gy/min. The irradiation dose causing an acute radiodermatitis was 30 Gy. The preparation in the form

TABLE 4

Results of a comparative evaluation of radioprotective effect of the preparation according to the present invention with known preparations upon a local X-ray irradiation of the skin in the dose of 30 Gy

| Nos 1 | Test compound 2 | Number of animals 3 | Reduction of duration of radiation response stages, % | | Total weighed evaluation on, % 6 |
|---|---|---|---|---|---|
| | | | erythema 4 | moist desquamation 5 | |
| 1. | Control | 7 | — | — | — |
| 2. | Preparation of the invention, 2,5% on a hydrophilic base | 7 | 38.8 | 62.8 | 51.3 |
| 3. | Preparation of the invention, 5% on a colloidal base | 7 | 25.9 | 58.9 | 46.4 |
| 4. | Preparation of the invention, 5%, on castor oil | 7 | 42.0 | 60.0 | 53.0 |
| 5. | Preparation of the invention, 5% on vaseline | 7 | 21.0 | 31.0 | 35.4 |
| 6. | Preparation of the invention, 5%, on lanolin | 7 | 42.0 | 52.0 | 42.4 |
| 7. | Ionol | 7 | 28.0 | 43.0 | 37.85 |
| 8. | Dimethylsulphoxide | 7 | — | 30.0 | 22.5 |
| 9. | Cystamine | 7 | 58.0 | 52.0 | 39.0 |
| 10. | Eugenol | 6 | — | 36.0 | 27.5 |
| 11. | Castor oil | 6 | 38.0 | — | 7.6 |

As it follows from the Table, the specific activity of the preparation according to the present invention in most cases is superior in effectiveness of known preparations upon a local application thereof.

of a 5% ointment was applied onto the skin after irradiation daily for 15–20 days till a complete healing of the skin. As the control preparation a 10% methyluracyl ointment was used. The control was effected in parallel without application of the preparations onto the skin. The severity of dermatitis was evaluated using the following tests: duration of erythema, duration of periods of dry and moist desquamation, duration of the entire period of regeneration by way of observations over a clinical progress of the radiation injury. The observations were effected daily during one month's period till a complete clinical recovery of burning lesions and were recorded by means of codes, individually for every animal, statistically treated and assessed using Student's criterion. The results of the tests are shown in Table 5 hereinbelow.

A daily regular applications of the preparation according to the present invention beginning with the irradiation moment and up to a full recovery of the skin makes it possible to substantially (by 17%) reduce the recovery period duration and to accelerate the skin regeneration process (see Table 5). Edema, inflammatory alterations in the skin subjected to irradiation are diminished after greasing with the preparation according to the present invention, erythema becomes less intensive, gets extinguished and passes into a light desquamation.

TABLE 5

Results of the study of a therapeutic effect of the preparation according to the present invention upon a local X-ray irradiation in the dose of 30 Gy

| Test compound 1 | Number of loci 2 | Total duration of the response, days 3 | Duration of the reaction, days Desquamation | | Reduction in duration of moist desquamation, % |
|---|---|---|---|---|---|
| | | | dry 4 | moist 5 | 6 |
| 1. Control | 14 | $10.8 \pm 0.2$ | $3.0 \pm 0.3$ | $3.4 \pm 0.2$ | — |
| 2. Preparation of the invention (5% ointment) | 14 | $9.7 \pm 0.2^x$ | $4.0 \pm 0.2^x$ | $1.1 \pm 0.2^{+x}$ | 67.7 |
| 3. Methyluracyl ointment (10%) | 14 | $11.0 \pm 0.3$ | $3.1 \pm 0.2$ | $2.4 \pm 0.4^x$ | 29.4 |

Note:
differences are statistically certain:
+ with control;
x with methyluracyl ointment; $P < 0.5$ The degree of wet desquamation is also sharply reduced; in half of the animals it is fully abesent, whereas in the control it is observed in 100% of the animals. In those cases where moist desquamation is, nevertheless, developing it is of a superficial character and the skin rapidly epithelizes. The treatment with the preparation according to the present invention started in proper time (prior to the development of an exsudative edema) prevents the formation of vesicles, the development of moit desquamation and ulceration of the skin. The period of moist desquamation, as determined for the group of animals on the average, is reduced by more than 3 times (see Table 5).

Thefore, against the background of the treatment with the preparation according to the present invention radiodermitis proceeds in an easier form and, instead of heavy clinical syndroms (erythema, edema, moist desquamation), it is manifested in a dry peeling of epiderm. As it is seen from Table 5 the effectiveness of the preparation according to the present invention, regarding an average duration of the moist desquamation period, is superior to the effectiveness of methyluracyl ointment by more than 2 times.

The effect of the preparation according to the present invention on the regression of an experimental tumor induced by an X-ray irradiation was also studied. The experiment was effected using 21 random-bred albino rats aged 8–12 weeks grafted with Walker-256 sarcoma into the hind limb pad 3 days before irradiation. A short-focus local irradiation of the tumor was effected using an X-ray unit at the anode voltage of 38 kV, current of 50 μA and filter of 0.4 mm Al. The effective radiation energy under these conditions is 20 keV, the half-attenuation layer is 12 mm. At the skin-focus distance of 6 mm, dose rate of 4.4 Gy/min, the tumor size of about 5 mm a uniform distribution of the dose is ensured. The surface dose of radiation is 20 Gy.

20 minutes prior to irradiation the skin was greased with the preparation according to the present invention. Observation over the tumor growth was carried out for 21 days (from the vaccination date), i.e. 18 days from the irradiation day; the tumor volume being measured and skin response determined on a daily basis. The test results have shown that the tumor regression in the control and in the experiment with an ointment base is pronounced since the 8th day, while in the experiments with the preparation according to the present invention—since the 4th day. Minimal volumes of tumors in the control differed from the initial one by 25%, while in the experiments with the preparation according to the present invention—by nearly 40%. The renewal of the tumor growth in the experiment with the preparation according to the present invention occured later and less intensively than in the control. As it has been experimentally shown, the preparation according to the present invention upon external application did not provide a radioprotective effect on the tumor tissue upon radiation therapy and did not facilitate the growth of the tumor during the period of its renewal. On the 18-th day all tumors were of nearly the same volume. the renewal of the tumor growth in the control and in experiments with an ointment base took place in 100% of cases, whereas in experiments with the preparation according to the present invention—in 83% of cases.

The effect of the preparation according to the present invention on the structure of the surface of regenerating epiderm of rats' auricles was studied by microscopic investigation, during their lifetime, by using a contact luminiscent microscope. The tests were carried out on 12 animals 2 months after a β-irradiation of the skin in the dose of 60 Gy.

Observation and photography of the skin were performed in the light of proper luminescence and upon staining with fluorescein in the dilution of $10^{-4}$. The lifelong investigation has made it possible to reveal a number of distinctions in the development of radiation dermal injuries in the case of using the preparation according to the present invention. In an early stage of the skin lesion these distinctions consisted in a various-degree desquamation of epiderm, while in a latter stage they were determined by the completeness and quality of healing of the wound surface and by the condition of epithelial regenerate. In the animals protected by the preparation according to the present invention the configuration and disposition of cornual squamae were more regular and properly arranged. In the skin loci non-protected by the preparation according to the present invention the disposition of cells was of a random character. In addition to thinned skin regions there were observed piling-up or building-up of cellular masses, the wound surface was tuberous, the shape of cells (cornual squamae) was polymorphic. Differences were also observed in the state of skin appendages. Thus, in the protected regions hairs remained and regenerated more rapidly, while in the non-protected regions hairs disappeared and did not recover during the observation period. Irradiation caused changes also in superficial skin vessels which are manifested in their non-uniform expansion and narrowing, convolution, twistedness, distensions and interruptions.

The superifical capillary network of the skin can be clearly revealed in polarized light. In the regions protected by the preparation according to the present invention the capillary loops had a more regular arrangement than in the regions subjected to irradiation without any preliminary treatment with the preparation of this invention.

Histological studies were carried out by light microscopy of skin sections of 28 rats subjected to a local irradiation with a preliminary treatment of the skin with the preparation according to the present invention. The investigation was initiated 30 and 70 days after irradiation when the process of healing of the radiation injuries was substantially completed and no macroscopic skin injuries were observed. The skin of irradiated loci did not differ visually from the adjacent tissues or in some cases had a cyanotic shade. The animals were killed by ether. Dissected regions of the skin of soles and ears with the area of 1 cm$^2$ were fixed in the Carnoy mixture and embedded into celloidin-paraffin. Sections of 5 $\mu$m thickness were stained with hematoxyline-eosin. The study has shown the presence of residual changes in tissues of the skin of ears of the irradiated animals. Thus, 2 months after $\beta$-irradiation the total thickness of the skin, as compared to the control, was decreased, atrophic, epithelium hyperplastic in some places. Appendages were absent. In the skin of ears greased with the preparation according to the present invention prior to irradiation the deviations from the normal structure were less pronounced, the phenomena of hyperplasia or aplasia of epiderm were not noted; cellular polymorphism, atrophic and degenerative changes in kerationcytes were less pronounced. The skin appendages were less injured, a part of them was fully intact.

The study of preparations of the paw skin has shown that one month after irradiation in the dose of 30 Gy no full normalization occurred in the regenerating skin structures in the regions non-subjected to a preliminary treatment with the preparation according to the present invention. The disturbance of the process of differentiation of the cellular structure was observed, the number of mytotically dividing cells was lowered. Pathological mitosises were encountered, as well as pyknotized cells duing in mitosis. The disturbance of processes of cell multiplication was also demonstrated by an increased number of binucleotic cells. In the majority of cells nuclei were degeneratively changed, and nucleoli were shrivelled or deformed. Degenerative changes were also observed in cells of the terminal sections of sweat glands and in the derm as well. Sharply decreased were cellular structure of the papillary layer, there were observed atrophy and atony of vessels, hemostasis phenomena were also noted.

In animals whose skin was preventively greased with the preparation according to the present invention prior to irradiation, the defects in the skin structure were less pronounced, degenerative and dystrophic changes in the epiderm were absent, processes of cellular reproduction and differentiation occurred correctly, a better preservation of appendages was observed, cellular composition of the derm was more divesified and changes in the structure of vessels were less pronounced.

Cytomorphological studies of skin sections have been also carried out; they have shown that the use of the preparation according to the present invention ensures a higher preservation of the epiderm structures and appendages thereof, it also facilitates an earlier and full recovery of injured tissues. In the skin loci treated with the preparation according to the present invention, as compared to the control, a better preservation of cell ultrastructures was observed, in particular that of intracellular membranes, intensification of the processes of intracellular reparation also took place.

To find out penetration of the preparation according to the present invention through the skin, a special study has been carried out on 24 random-bred albino mice using the preparation of this invention labelled with $^{14}$C. The preparation's specific activity was 15,799 MBq/g. The preparation in the form of a 5% ointment was applied onto the sole skin. The animals were slaughtered after 0.2, 0.4, 3.0, 24.0, 72.0 hours and 10 days. The content of $^{14}$C was radiometrically determined in blood samples.

It has been shown that the content of $^{14}$C in all samples is less than sensitivity of the procedure employed, i.e. 37 Bq in the sample which can be associated with both a low resorption of the preparation through the skin and with a rapid mobilization thereof from blood.

As it has been shown by the study of adsorption of the preparation according to the present invention carried out on 24 rats in order to investigate the skin route of its penetration into the organism, the basic stage of its resorption by the skin is developing within 2 hours after application of the preparation according to the invention, whereafter the resorption speed is sharply decreased. This is characteristic for processes of saturation of the skin and makes it possible to assume the absence of a resorptive effect due to penetration of the preparation of this invention into the blood flow. The maximum degree of accumulation is 80 $\mu$g/cm$^2$ after 10 hours of exposure which is sufficient for manifestation of the local biological effect.

Since the leading role in the pathogenesis of thermal death of cells is played by processes of injury of cellular membranes, the preparation according to the present invention has been tested for feasibility of its use as an antiburning preparation. The antiburning effect of the preparation according to the present invention was studied on random-bred albino rats of both sexes with a mass of 230–250 g in the number of 80. A thermal burn of the back skin (with a preliminary depilation) was induced by means of an electric heater having a circular contact field of 1 cm diameter (the contact field area was 0.79 cm$^2$). The contact plate of the electric heater had the temperature of 200° C., the exposure time—10 seconds. The mechanical load applied to the animal's skin during application of a burn was constant and equal to 19.0 g/cm$^2$. As judged by the clinico-histological assessment, the severity of the thus-produced injury corresponded to a III degree burn.

The course of treatment of the animals was started directly after effecting an experimental burn and continued till a complete healing of the wound surface. The injured skin regions were daily coated, by means of a spatle, with a thin layer of an ointment of the preparation according to the present invention in an amount of about 50 mg/cm$^2$.

The ointments were prepared on lanolin or vaseline base with different content of the active principle. Tests of the preparation according to the present invention were carried out in comparison with the prior art preparations (panthenol, methyluracyl ointment—5 and 10%, dog-rose oil). Vaseline and lanolin were used as control. The test results are shown in Table 6 hereinbelow.

TABLE 6

Antiburning effectiveness of the preparation according to the present invention as by the criterion of reduction of the healing period duration as compared to the control and prior art preparations

| Experimental group | ♂ ♂ | | ♀ ♀ | |
|---|---|---|---|---|
| | Healing period (days) | Stimulant effect, % | Healing period (days) | Stimulant effect, % |
| Control I (vaseline) | 32.8 ± 4.0 | — | 36.8 ± 6.8 | — |
| Control 2 (lanolin) | 33.1 ± 3.5 | — | 36.5 ± 6.5 | — |
| Panthenol | 29.7 ± 4.3 | +10.3$^{xx}$ | 36.0 ± 7.0 | +2.2$^x$ |
| Dog-rose oil | — | — | 31.9 ± 4.5 | +13.3$^x$ |
| methyluracyl ointment, 5% | 37.2 ± 6.1 | — | — | — |
| methyluracyl ointment, 10% | 34.5 ± 5.0 | — | — | — |
| 5% preparation of this invention | 26.7 ± 2.8 | +19.3$^{xx}$ | 31.5 ± 5.8 | +14.4$^x$ |
| 10% preparation of this invention | 27.5 ± 3.4 | +16.9$^{xx}$ | 33.1 ± 6.7 | +10.1$^x$ |

Note:
$^x$effect is assessed relative to control I
$^{xx}$effect is assessed relative to control 2 process—on the 20-25-th day of the experimental observation.

According to the obtained results, the effectiveness of the preparation of the present invention in a 5% concentration is superior to the effectiveness of the prior art preparations.

The preventive and therapeutic effects of the preparation according to the present invention were studied on dermatitis caused by UV-irradiation. The experiments were carried out on 38 random-bred albino male rats aged 4–5 months with the mass of 310 g.

6 groups of animals were subjected to irradiaton. The soles of test rats (2, 4 and 5-th groups) were greased with the preparation according to the present invention in the form of a 5% ointment on vaseline base 30 minutes prior to irradiation and immediately thereafter. In rats of groups 5 the greasing was effected daily till a full healing of burns. The animals of groups 1 and 3 served as control. The hind limbs of the animals were rigidly secured, by means of a special adaptor, at the distance of 24 cm from a quartz lamp so as to ensure standard irradiation conditions. Subjected to irradiation were skin regions of 90 mm$^2$ on each paw. An UV-irradiation was effected by means of a gas-discharge quartz lamp with a radiation spectrum of 230–260 nm with the maximum at 254 nm. The exposure dose rate was 16 J/m$^2$. The soles of rats of groups 1 and 2 were irradiated for 15 minutes; those of rats of groups 3, 4 and 5—30 minutes, group 6—45 minutes.

The assessment of the degree of the protective effect was effected on the basis of visual observation over the clinical progress of the dermatitis. The observations were carried out for 24 days till a complete clinical healing of the skin injuries and recorded by the commonly accepted method (in points) using a 6-point scale. Then single readings were summed up for every animal. The resulting values were statistically processed and assessed by means of Student's t-criterion. Therefore, the severity of dermatitis was assessed by the following parameters: duration of weak and intense erythema, dry and moist desquamation. The test results are shown in Table 7 hereinbelow.

TABLE 7

Results of studies of the protective effect of the preparation of this invention on skin of rats' paws upon a UV-irradiation in different dose

| Nos 1 | Test preparation 2 | Irradiation dose 3 | Number of rats 4 | Number of loci 5 | Duration of the response (days) X ± m | | | |
|---|---|---|---|---|---|---|---|---|
| | | | | | Erythema | | Desquamation | |
| | | | | | weak 6 | intense 7 | dry 8 | moist 9 |
| 1. | Control | 16 J/m$^2$ | 6 | 10 | 1.2 ± 0.4 | 1.8 ± 0.4 | 2.4 ± 0.5 | 2.3 ± 0.6 |
| 2. | Preparation of this invention (5% ointment) | 15 minutes | 6 | 12 | 2.4 ± 0.4 | 1.2 ± 0.3 | 1.2 ± 0.5 | 0.7 ± 0.3$^x$ |
| 3. | Control | | 7 | 13 | 0.3 ± 0.08 | 0.8 ± 0.08 | 6.7 ± 0.4 | 3.2 ± 0.4 |
| 4. | Preparation of this invention (5% ointment) for prophylaxis | 16 J/m$^2$ 430 minutes | 5 | 10 | 1.5 ± 0.3 | 2.1 ± 0.4 | 2.1 ± 0.5 | $^x$1.1 ± 0.3$^{xx}$ |
| 5. | Preparation of this invention (5% ointment) for treatment and prophylaxis | | 7 | 14 | 0.7 ± 0.16 | $^x$0.8 ± 0.16 | 5.0 ± 0.7 | $^x$1.0 ± 0.16$^{xxx}$ |
| 6. | Control | 45 minutes | 6 | 12 | 0.4 ± 0.2 | 1.1 ± 0.2 | 5.4 ± 0.8 | 3.3 ± 0.4 |

Note:
$^x$differences statistically valid (P < 0.5) relative to control group 1
$^{xx}$differences statistically valid (P < 0.001) relative to control group 3

The stimulant effect of the preparation according to the present invention expressed in reduction of the wound surface area at a single-time use thereof is most clearly pronounced in the final stage of the healing The preventive application of an ointment of the preparation according to the present invention upon a 30-minutes' irradiation quite noticeably lowers the manifestation of the bullous stage and the number of ulcers.

The response becomes substantially less pronounced than in the case of the dose obtained over 15 minutes (Table 7) and, hence, the factor of dose variation according to the moist desquamation criterion is above 2. The erythemic response upon a preventive application of the ointment under these conditions is retained.

A repeated therapeutic and preventive application of the ointment not only prevents the skin from moist desquamation and formation of vesicles, but also enables a considerable diminution of manifestation of the erythemic response and retaining the duration of this stage unchanged. It should be noted that in the case of application of the ointment of the preparation according to the present invention for therapeutic and preventive purposes the intensity of erythema induced by a 30 minutes' irradiation becomes smaller than that of a 15 minutes' irradiation in the control, whereas the response to a UV-irradiation is revealed only in dry peeling of the epiderm.

The acute toxicity of the preparation according to the present invention was studied on random-bred albino mice of 18–23 g mass, random-bred albino rats of 200 g mass and on dogs upon a single-time administration of the preparation.

The preparation according to the present invention was administered intragastrically or intraperitoneally in several doses, each dose being studied on 6 animals. The test animals were observed for 10 days.

The effect of the preparation according to the present invention on dogs was studied in the dose of 12,000 mg/kg. The preparation according to the present invention was introduced into the dogs' stomach after a 18-hour starvation.

The test results are shown in the following Table 8.

TABLE 8

Acute toxicity of the preparation according to the present invention

| Mode of administration | Animals | LD$_{50}$, mg/kg |
|---|---|---|
| Intragastrically | mice | above 32,000 |
| Intragastrically | dogs | above 12,000 |
| Intraperitoneally | mice | above 30,000 |
| Intraperitoneally | rats | above 16,000 |

The study of chronical toxicity of the preparation according to the present invention upon its repeated use was carried out in experiments on young white male rats with the initial average mass of 197 g. The rats were placed in cages with 15 animals in each. The preparation according to the present invention was mixed with a small amount of milk and was given in the morning to rats, whereafter the animals were given water and food. The preparation according to the present invention was administered to the rats the in the following doses:

Group I—control: no preparation was given to the rats; Group II—2 mg/kg; Group III—20 mg/kg; Group IV—200 mg/kg.

The experiment was carried out for 6 months during which period the animals were assessed for their general condition, behaviour and feed consumption.

The following parameters were taken into consideration: mass of the animals—by daily weighing the rats; state of the peripheral blood—the content of hemoglobin, number of erythrocytes and leukocytes and leukycytic formula were determined. In order to assess the effect of the preparation according to the present invention on the functional state of liver and kidneys, the content of sugar and that of residual nitrogen in blood was determined 4 and 6 months after the beginning of the experiment, the activity of alanine- and aspratate-aminotransferase (AlAT and AsAT) in blood serum, liver homogenates and urine of white rats after 4 and 6 months, activity of alkaline phosphatase after 6 months, the content of total protein and its fractions in blood serum. Furthermore, after 4 and 6 months a clinical investigation of urina for the content of protein, sugar, pH and sediment composition was also carried out.

At the end of the experiment the rats were decapitated and the inner organs were weighed to determine the mass coefficient, whereafter the organs were subjected to a histological analysis.

The test results have shown that during the experiment no changes of the general state of the test animals were observed. In the doses as used in the experiment the preparation according to the invention provided no effect on behaviour of the animals, their growth and feed consumption.

The content of hemoglobin in carrying out the experiment first increased in all rats as compared to the initial level starting with the 3-rd month; no differences in the control and test rats were observed (P<0.5). Biochemical analyses of the functional state of the liver and kidneys revealed no essential difference in characteristics of the control and test groups.

The effect of a repeated adminstration of the preparation according to the present invention was studied on dogs for 3.5 months. The dogs were given the preparation orally prior to feeding in the doses of 20 and 200 mg/kg. During the experiment the dogs were monthly weighed and tested for morphology of the peripheral blood, enzymological and proteinological analyses, as well as clinical analysis of urine caccording to the procedures employed in the above-described experiments on rats.

During the entire period of observations no deviations in the animals' behaviour and mass thereof were noticed.

No toxic effect of the preparation according to the present invention has been revealed in these experiments on the dogs' organism upon a repeated peroral administration of the preparation in the doses of 20 and 200 mg/kg.

In a separate series of experiments on white mice and rats the toxic effect of metabolites of the preparation according to the present invention (oxidized form, products of hydrolytical cleavage of esterial groups in the third and fifth positions and oxidation of one of methyl groups in the second or sixth positions) was studied.

It has been found that upon a single-time (doses of from 10,000 to 20,000 mg/kg) and repeated (doses of 2, 10, 20 mg/kg) peroral administration of primary oxidation metabolites of the preparation according to the present invention to animals during 5–6 months no visible signs of intoxication as well as essential deviations surpassing the normal physiological limits were observed in mass dynamics, in the content of hemoglobin, erythrocytes, leukocytes, leukocytic formula of the peripheral blood, in characteristics of a biochemical analysis of blood: residual nitrogen, sugar, total protein, protein fractions, activity of enzymes AlAT, AsAT, alkaline phosphatase and coefficients of mass of the inner organs which would be associated with the effect of the above-mentioned compounds.

Upon a peroral administration of the preparation according to the present invention to rats during critical periods of embryogenesis and during the entire pregnancy period no teratogenic and embryotoxic effects were observed.

The preparation according to the present invention upon a repeated administration to mice and rats perorally or by way of hypodermal injections revealed no carcinogenic activity. In experiments on *Dr. melanogaster* the preparation according to the present invention produced no mutagenic effect. The preparation according to the present invention was also studied for its distribution in the animal's organism and withdrawal therefrom. The test results have shown that ½ portion of the preparation of this invention is excreted with stools. 50% of the preparation of the invention are absorbed in the blood out of which amount 37.9% are withdrawn with urina, 1.5%—with the breathed out air, the remainder—through other routes.

The preparation according to the present invention was studied in clinic. The clinical tests of the preparation according to the present invention were carried out on 134 patients with different oncological diseases (mammalian gland cancer, skin neoplasms, cervical and rectal carcinoma, lymphosarcoma, lymphogranulometosis, nasopharynx carcinoma, sarcoma and the like) subjected to a radiation therapy on 307 skin field. The tests were carried out on patients of different sexes and age, in various stages of the main disease and different localizations of the tumor process and, hence, of skin injuries at different kinds of the radiation therapy. The test patients aged 35 to 60 years.

During the tests various modes of application of the preparation according to the present invention have been studied, as well as various dosage rates and optimal control procedures have been elaborated. Groups of patients were chosen with the account of age and tumor location in order to ensure comparability of the test results.

Particular objectives of these studies were: (a) assessment of the frequency of occurrence of skin responses in comparable groups of patients administered with the preparation according to the present invention; (b) analysis of the degree of manifestation of skin responses in the same groups of patients; (c) assessment of the total irradiation dose which is a threshold dose in respect of manifestation of responses in the group of patients subjected to applications of the preparation of this invention.

The preparation according to the present invention was administered as applications prior to irradiation and thereafter. There has been tested and proven to be the most effective the treatment scheme with a 2-times' and 3-times' administration of the preparation a day. The results of the clinical study were assessed according to subjective and objective characteristics. The objective characteristics involved medical examination of the dynamics of radiodermatitides, manifestation and duration of such radiation responses as erythema, edema dry and moist epidermitises, pigmentation, baldness, speed of recovery of injuries. The subjective characteristics included the patients' assessment regarding the intensity of pain feelings prior to and after administration of the preparation, as well as skin perceptions such as itching, burning and their change under the effect of the preparation according to the present invention. Improvement was assumed in the cases where a positive dynamics of objective and subjective characteristics was noted together with reduction of skin responses duration or with diminution of their intensity upon a positive subjective assessment by the patients.

Without the availability of objective positive shifts in the course of radiodermatitis the results were not assessed as improvement. At a negative response of a patient to the preparation according to the present invention no assessment was made.

The results of clinical tests are shown in Tables 9 and 10 hereinbelow.

TABLE 9

| | | Clinical characteristics of patients administered with the preparation of the invention | | | | | |
|---|---|---|---|---|---|---|---|
| Nos 1 | Objective of administration of the preparation 2 | Diagnosis 3 | Number of patients 4 | Number of test fields 5 | Number of control fields 6 | Mean total dose, average schedule dose (Gy) 7 | Characteristic of the produced effect 8 |
| 1. | Prophylaxis | Lymphogranulomatosis(three schedules of fractionation) | 32 | 64 | 64 | 35–46 Gy (2.5–1.4 Gy) | Diminished pain syndrome, lessened manifestation of response (weak erythema, dry desquamation) |
| 2. | | Mammalian gland | 4 | 12 | 0 | 75 Gr (10–15 Gy locally) | Pronounced protective effect |
| 3. | | cancer with pronounced accompanying diseases | 22 | 22 | 21 | 35–46 Gy (1.5–2.0 Gy) | Diminished response |
| 4. | Therapy and | Rectal carcinoma | 15 | | | 90 Gy (grid) | Clearly marked effect: |
| 5. | prophylaxis | Lymphogranulomatosis | 13 | | | 45–35 Gy | diminished erythema, |
| 6. | | Mammalian gland | 29 | 82 | 39 | (1.5–2.5 Gy) | no progress of |
| 7. | | Nasopharynx carcinoma | 6 | | | 32–40 Gy (2.4 Gy) | dry epidermitis into the |
| 8. | | Lymphosarcoma | 5 | | | 32–42 (2.4 Gy) | wet stage, reduced itching and |
| 9. | | Lung cancer | 1 | | | 35–45 Gy | burning, lowered |
| 10. | | Cervical carcinoma | 4 | | | (1.5–2.5 Gy) | pain syndrome |
| 11. | Therapy | Late radiation skin pathologies (indurative changes with pronounced pain syndrome) | 2 | 2 | 0 | | Positive effect (lessened edema and diminished pains) |

TABLE 9-continued

Clinical characteristics of patients administered with the preparation of the invention

| Nos 1 | Objective of administration of the preparation 2 | Diagnosis 3 | Number of patients 4 | Number of test fields 5 | Number of control fields 6 | Mean total dose, average schedule dose (Gy) 7 | Characteristic of the produced effect 8 |
|---|---|---|---|---|---|---|---|
| 12. | | Electrical burning | 1 | 1 | 0 | | Clearly pronounced |
| 13. | | TOTAL: | 134 | 183 | 124 | | |

TABLE 10

Therapeutic effect of the preparation of the invention on the skin at radiation dermatitides

| | | | | Experimental fields | | Control fields | |
|---|---|---|---|---|---|---|---|
| Nos 1 | Response type 2 | Characteristics of radiation responses of skin 3 | Number of patients 4 | Response after treatment, during and after the course of radiation therapy 5 | Number 6 | Skin response during and after radiation therapy 7 | Number 8 |
| 1. | Acute radiation injuries | Marked dry epidermitis, initial phenomena of wet epidermitis | | Rapid epithelization of foci of moist epidermitis, reduced erythema, increased pigmentation | 16 | Transition to phenomena of moist epidermitis, increasing eythema | 13 |
| 2. | | Pain phenomena, burning. Erythema with pain syndrome | 73 | Reduced erythema, arrest of pain syndrome, lessened burning | 24 | Increasing erythema with phenomena of moist epidermitis accompanied by pain syndrome | 18 |
| 3. | | Phenomena of indurative edema of soft tissues with pronounced pain syndrome | | Reduced edema, disappearance of pain syndrome | 2 | Increasing indurative edema, enhancing pain syndrome, itching | 2 |
| 4. | Late radiation injuries | Pain syndrome, soft tissues edema, dense induration | 2 | Reduced intensity of pain feelings and edema, lesser induration density | 2 | | |

The results of the tests performed have proven the previously experimentally found presence of readioprotective and therapeutical effect in the preparation according to the present invention. A pronounced aeffect observed in the tests is manifest at irradiation doses of not less than 40 Gy (Grays) upon a single-time administration. At the same time, upon a preventive daily 3-times' administration of the preparation according to the present invention the responses reached the stage of dry epidermitis in a dose of 40-44 Gy and in this case no such pain feelings as skin itching and burning were noted. However, in the control group of patients in the case of the same doses initial phenomena of moist epidermitis were observed which was the reason of discontinuation of the radiation therapy. In the group of patients with phenomena of pronounced dry epidermitis the therapeutic effect was revealed after two or three treatments with the preparation according to the present invention as a reduced edema, extinction of pain feelings, reduced erythema and enhanced pigmentation. After 4-5 days there was noted a substantially total peeling of the pigmented epithelium with cleaning of an intact skin thereunder. The treatment was carried on locally in fields of a smaller size. The total focal dose was brought to 65-70 Gy without increasing degree of manifestation of radiation responses against the background of the continued treatment with the preparation according to the present invention. In the non-treated control regions the intensity of radiation responses was growing and reached the stage of a focal wet epidermitis which was the cause of a forced break in the radiation treatment. In the group of patients with phenomena of a focal wet epidermitis the treatment with the preparation according to the present invention also was carried out three times a day, but against the background of discontinued radiation therapy. A rapid epithelization of the foci of moist epidermitis and disappearance of pain feelings was noted. In a number of patients having large areas of epiderm desquamation a non-intensive short-time feeling of itching was noted after initial treatment procedures. All phenomena of moist epidermitis were arrested during a week's time and the patients completed the radiation therapy at planeed doses.

A positive therapeutical effect of the preparation according to the present invention in patients with late radiation changes was characterized by a reduced intensity of pain feelings, lowered edema and a lesser density of induration. This improvement points to a high effectiveness of the preparation according to the present invention at such severe pathology which is exemplified by late radiation injuries. Though the treatment with the preparation according to the present invention did not fully arrest the pathological process, the above-mentioned clinical ameliorations in the stages usually resistant to the treatment support the experimental data regarding an improved course of metabolic processes in the injured skin.

Also important is questioning of the patients to find out their subjective assessment of the effect produced by the preparation according to the present invention. The practice of taking daily notes by the patients was used to put down their own feelings prior to and after administration of the preparation according to the present invention.

Clinical tests helped to reveal a new property of the preparation according to the present invention—a clearly pronounced analogetic effect: 15-30 minutes after application of the preparation on injured skin regions the itch and pain syndromes are sharply reduced or pass fully. This effect is retained for 6-8 hours and prolonged by repeated applications of the preparation which ensures a high level of a psychological acceptance of the composition according to the present invention by patients.

An electron-microscopy investigation of operation biopsies of female breast skin subjected or not to a radiation therapy for mammalian gland cancer. The irradiation (tele-gamma-therapy) of the mammary gland was effected following a standard procedure tangentially at two opposite fields, one field a day. The single dose was 2.6 Gy, to total dose—60 Gy and more. The preparation according to the present invention was applied in a thin layer onto the skin surface prior to each irradiation 30 minutes before the procedure. A group of patients with the skin non-treated prior to irradiation served as control.

As it has been shown by electron-microscopy investigations of the biopsy material, upon a repeated application of an ointment of the present invention onto a healthy non-irradiated skin no deviations in the structure of epidermal cells occur. In patients subjected to a course of a radiation therapy without using any protective agents residual changes are observed in the epiderm: swelling and edema of nuclei, expansion of the perinuclear space, nuclei hyperplasia, thinning of organoids in cells, appearance of fusion foci in cytoplasm. Also noted is the disturbance of the process of keratinocyte differentiation process associated with the formation and orientation of tonofibrillae—the latter are formed less intensively and arranged in a random fashion. A very indicative feature of radiation dermatitis is edema of intercellular bridges and structural changes in desmosomes. A preventive application of an ointment of the preparation according to the present invention makes it possible to avoid the development of radiation injuries of the skin. The integrity and continuity of the nuclear membrane is retained, no fusion foci are present in cytoplasm, differentiation of cells occurs according to its regular law, tonofibrillae are arranged into dense strands which are uniformly distributed in cytoplasm. Intercellular bridges and desmosomes are not destroyed, no signs of edema are observed.

Therefore, the clinical studies have shown that a proper-time administration of the preparation according to the present invention makes it possible to substantially (by more than 2 times) reduce frequency of appearance of radiation responses of the skin at a dose of up to 40 Gy; at greater doses it lowers the degree of manifestation of skin responses preventing the appearance of wet dermatitis. These data enable a conclusion that a total threshold dose of irradiation for a preventive effect of the preparation according to the present invention are doses of 40-45 Gy; the total threshold dose for a therapeutic effect is the dose of 70 Gy. Such properties as analgetic and anti-itching effect have been also revealed in the preparation according to the present invention after clinical tests. The administration of the preparation according to the present invention makes it possible to carry out a planned radiation therapy without obligatory intervals due to a reduced frequency and degree of manifestation of radiodermatitides which may contribute to a higher effectiveness of the treatment.

Therefore, as it has been shown by experimental and clinical studies, the preparation according to the present invention has a clearly pronounced local radioprotective effect on the skin and reliably protects the same from radiation injuries at therapeutical irradiation doses. Taking into account a low toxicity of the preparation, its tropism to the skin, a low degree of resorption at a dermal route of penetration into the organism, absence of a protective effect on a tumor revealed thereupon lack of any other contridications against application, the preparation according to the present invention possessing a broad range of pharmacological properties is advisable for both prophylaxis and treatment of skin injuries in clinics of radiation therapy and for protection of the skin of professional roentgenologists, as well as for prevention and treatment of home UV and thermal burns of the skin.

The preparation according to the present invention is administered as a 5 or 10% ointment.

The preparation according to the present invention in the form of an ointment is manufactured by a conventional procedure. The active principle—2-,6-dimethyl-3,5-diethoxycarbonyl-1,4-dihydropyridine can be prepared following the method described hereinbelow. Hexamethylenetetramine, ammonium acetate and ethyl acetoacetate are dissolved in isopropanol, heated to reflux and boiled upon stirring in a water bath. After cooling of the reaction mixture the resulting precipitate is washed and recrystallized. The desired product is thus obtained. The preparation according to the present invention is used in the following manner. For preventive purposes a 5% ointment of the preparation according to the present invention is applied onto the skin in the zone of a planned irradiation 30-40 minutes prior to the irradiation seance. After irradiation the skin is again greased with the preparation according to the present invention with intervals of 1-2 hours and then the skin is greased daily 2-3 times a day. Upon a repeated irradiation the skin greasing is effected before each seance 30-40 minutes prior thereto, after each seance and then three times a day on a daily basis over the entire course of treatment and during the subsequent 5-10 days.

For therapeutic purposes use is made of a 5% or 10% ointment of the preparation according to the present invention in the case of appearance of radiation injuries of the skin. The ointment is applied in a uniform layer onto the injured skin regions daily 3 times a day. The treatment is effected till healing of the skin and disappearance of pain symptoms and itching. The treatment course is 10-20 days depending on severity of the injury.

In individual patients during the first 30 minutes after application of the preparation onto the skin skin a feeling of a slight burning of the skin may appear which rapidly passes and is not a contraindication against its administration. No contraindications for the preparation of this invention have been revealed.

What is claimed is:

1. A preparation for external local application to the skin for the prevention and treatment of skin radiation burning lesions in the form of an ointment, comprising, as the active principle, from 5 to 10% by weight of 2,5-dimethyl-3,5-diethoxycarbonyl-1,4-dihydropyridine of the following formula:

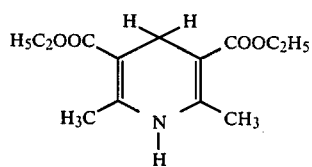

and a pharmaceutically acceptable diluent.

2. A preparation as claimed in claim 1 which comprises, as the pharmaceutically acceptable diluent, an ointment base comprising petroleum jelly or lanolin.

3. A method for the prevention and treatment of radiation damage to the skin in a host caused by both ionizing the nonionizing radiation, which comprises contacting the skin of said host with an effective radiation inhibiting amount of a pharmaceutical preparation comprising as an active principle, 2-6-dimethyl-3,5-diethoxycarbonyl-1,4-dihydropyridine of the following formula:

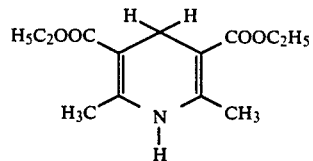

and a pharmaceutically acceptable diluent.

4. The method as claimed in claim 3 wherein the pharmaceutical preparation is in the form of an ointment and wherein the active principle is present in said ointment in an amount of from 5 to 10% by weight.

5. The method as claimed in claim 4 wherein the ointment comprises petroleum jelly or lanolin.

* * * * *